United States Patent [19]

Epple

[11] Patent Number: 5,180,841
[45] Date of Patent: Jan. 19, 1993

[54] PREPARATION OF 1-AMINO-2-CHLORO-4-HYDROXYANTHRAQUINONE

[75] Inventor: Gerhard Epple, Weisenheim, Fed. Rep. of Germany

[73] Assignee: BASF Aktiengesellschaft, Ludwigshafen, Fed. Rep. of Germany

[21] Appl. No.: 823,814

[22] Filed: Jan. 22, 1992

[30] Foreign Application Priority Data

Jan. 23, 1991 [DE] Fed. Rep. of Germany ....... 4101875

[51] Int. Cl.$^5$ .......................................... C07C 221/00
[52] U.S. Cl. .................................................. 522/244
[58] Field of Search ........................................ 552/244

[56] References Cited

U.S. PATENT DOCUMENTS 4,997,960 3/1991 Epple .................................. 552/244

FOREIGN PATENT DOCUMENTS 0361253 5/1990 European Pat. Off. .
2428337 12/1975 Fed. Rep. of Germany .
3832740 4/1990 Fed. Rep. of Germany .
0602882 4/1926 France .
0507065 6/1939 United Kingdom .
507065 6/1939 United Kingdom .

Primary Examiner—Marianne M. Cintins
Assistant Examiner—Kimberly J. Kestler
Attorney, Agent, or Firm—Oblon, Spivak, McClelland, Maier & Neustadt

[57] ABSTRACT

The useful dye intermediate 1-amino-2-chloro-4-hydroxyanthraquinone is prepared by chlorinating 1-amino-4-hydroxy-2,3-dihydroanthraquinone with chlorine in concentrated sulfuric acid.

3 Claims, No Drawings

PREPARATION OF 1-AMINO-2-CHLORO-4-HYDROXYANTHRAQUINONE

The present invention relates to a novel for preparing 1-amino-2-chloro-4-hydroxyanthraquinone I by chlorinating 1-amino-4-hydroxy-2,3-dihydroanthraquinone II.

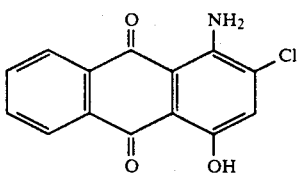

I

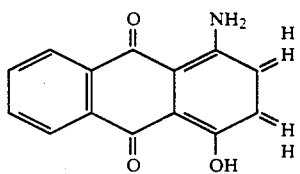

II

It is known from DE-A-38 32 740 that 1-amino-2-chloro-4-hydroxyanthraquinone can be prepared by chlorinating 1-amino-4-hydroxyanthraquinone III

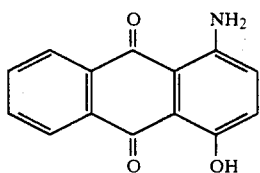

III in 90–100% aqueous sulfuric acid or in up to 2% oleum.

However, starting from 1,4-dihydroxyanthraquinone IV (quinizarine), the preparation of sufficiently pure III requires at least two synthesis stages, namely the conversion to 1,4-diamino-2,3-dihydroanthraquinone V (leukamine) in ammonia and subsequent conversion to III in sulfuric acid with manganese dioxide. The manganese dioxide makes it difficult to regenerate the sulfuric acid.

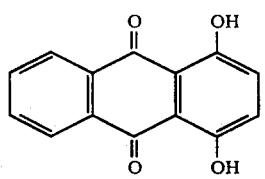

IV

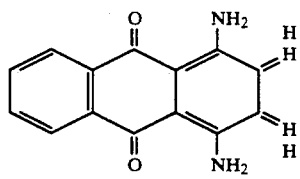

V

The preparation of II is known from French Patent 602,882 or British Patent 507,065.

In general, the process of the present invention is carried out by dissolving the starting material II in from 4 to 20 times, preferably from 6 to 10 times, the amount of 92–100%, preferably 96–99%, sulfuric acid with stirring and introducing chlorine at from 20° to 80° C., preferably at from 40° to 70° C., at least 2 mol of chlorine being necessary.

The course of the reaction is advantageously monitored by thin layer chromatography. The oxidation of II to III and the chlorination of III take place simultaneously. The reaction is interrupted when all of II and more than 97 % of III have been converted, either by pouring the reaction mixture into water or slowly adding water to the reaction mixture to precipitate the product.

1-Amino-2-chloro-4-hydroxyanthraquinone is an important intermediate in the preparation of red anthraquinone dyes, for example in the preparation of Disperse Red 60, C.I. 60756.

The process of the present invention will now be more particularly described by way of example.

EXAMPLE 1

500 g of 95% pure 1-amino-4-hydroxy-2,3-dihydroanthraquinone (II) are introduced into 3000 g of 97.5% sulfuric acid with stirring. The mixture is heated to 60° C. and 308 g of chlorine are passed in over 24 hours. Then nitrogen is passed through the reaction mixture for 2 hours to drive out dissolved hydrogen chloride.

Then 1220 g of water are added dropwise at 60° C. in the course of 3 hours, and the product precipitates. It is filtered off with suction, washed with 1500 g of 60% sulfuric acid and then washed neutral with water and dried.

Yield: 509.8 g of 92.3 % pure product, i.e. 87.3% of theory.

EXAMPLE 2

440 g of 90.9% pure 1-amino-4-hydroxy-2,3-dihydroanthraquinone (II) are dissolved in 2400 g of 97.4% sulfuric acid. Chlorine is introduced at 60° C. until only traces of 1-amino-4-hydroxyanthraquinone III are detectable by thin layer chromatography. Nitrogen is passed through for 2 hours, and then 960 g of water are added dropwise at 60°–90° C. over 2 hours. The reaction mixture is cooled down and the precipitated product is filtered off with suction. It is washed with 2000 g of 60% sulfuric acid, and then with water and dried.

Yield: 456.6 g of 90.9% pure product; i.e. 91.4% of theory.

EXAMPLE 3

80 g of 95.6% pure 1-amino-4-hydroxy-2,3-dihydroanthraquinone are dissolved in 506 g of 97.5% sulfuric acid and chlorinated as indicated in Example 2. The product is precipitated by the dropwise addition of 210 g of water and worked up as in Example 2.

Yield: 85.6 g of 96.5% pure product, i.e. 91% of theory.

EXAMPLE 4

1072 g of 93.3% pure 1-amino-4-hydroxy-2,3-dihydroanthraquinone are introduced into 6000 g of 97.5% sulfuric acid and heated to 60° C. 700 g of chlorine are introduced at 60°–65° C. in the course of 18 hours. Then nitrogen is passed through the reaction mixture in order to drive out dissolved hydrogen chloride.

Then 2400 g of water are added at 90°–95° C., which precipitates the product, which after cooling down to 20°–25° C. is filtered off and washed with sulfuric acid and water.

Drying leaves 1033 g of 92% pure 1-amino-2-chloro-4-hydroxyanthraquinone.

We claim:

1. A process for preparing 1-amino2-chloro-4-hydroxyanthraquinone, which comprises chlorinating 1-amino-4-hydroxy-2,3-dihydroanthraquinone with at least 2 mol of chlorine in concentrated sulfuric acid.

2. A process as claimed in claim 1, wherein from 4 to 20 times the amount of 92–100% sulfuric acid is used, based on the dihydroanthraquinone.

3. A process as claimed in claim 1, wherein the chlorination is carried out at from 40° to 70° C.

* * * * *